(12) United States Patent
Kamiya et al.

(10) Patent No.: US 8,576,087 B2
(45) Date of Patent: Nov. 5, 2013

(54) RADIATION IMAGING SYSTEM HAVING RADIATION IMAGING CASSETTE AND CONSOLE DEVICE, AND RADIATION IMAGING PROGRAM

(75) Inventors: Takeshi Kamiya, Kanagawa (JP); Yusuke Kitagawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 401 days.

(21) Appl. No.: 12/929,378

(22) Filed: Jan. 20, 2011

(65) Prior Publication Data

US 2011/0227750 A1 Sep. 22, 2011

(30) Foreign Application Priority Data

Mar. 16, 2010 (JP) ................................. 2010-058608

(51) Int. Cl.
*G08B 21/00* (2006.01)
(52) U.S. Cl.
USPC ............ 340/687; 340/2.1; 340/3.1; 340/3.21; 340/10.1; 340/539.29; 340/600; 340/686.1; 378/37; 378/74; 378/87; 378/162; 378/163; 378/164; 378/165; 378/166; 250/318; 250/370.08; 250/370.09; 250/336.1; 250/484.4; 250/363.04; 250/362; 250/363.07; 250/370.01; 250/505.1; 250/580; 250/341.1; 600/407; 600/416; 600/424; 600/425; 600/429; 600/459

(58) Field of Classification Search
USPC ................ 340/3.1, 540, 600, 687, 686.1, 2.1, 340/3.21, 10.1, 539.29; 250/370.09, 484.4, 250/580, 318, 370.08, 336.1, 363.04, 362, 250/363.07, 370.01, 505.1, 341.1; 378/37, 378/74, 87, 162, 163, 164, 165, 166; 600/407, 416, 424, 425, 429, 459
See application file for complete search history.

(56) References Cited

U.S. PATENT DOCUMENTS 5,369,759 A * 11/1994 Kanbe ............................. 714/2
5,650,623 A * 7/1997 Rajamani et al. .......... 250/336.1
(Continued)

FOREIGN PATENT DOCUMENTS

| EP | 2 025 288 A1 | 2/2009 |
| JP | 2004-298225 A | 10/2004 |

(Continued)

OTHER PUBLICATIONS

Notice of Reasons for Refusal issued by Japanese Patent Office on Aug. 7, 2013 in Japanese Patent Application No. 2010-058608 which corresponds to the present application.

*Primary Examiner* — George Bugg
*Assistant Examiner* — Paul Obiniyi
(74) *Attorney, Agent, or Firm* — Jean C. Edwards, Esq.; Edwards Neils PLLC

(57) ABSTRACT

A radiation imaging system includes a radiation imaging cassette and a console device. A communication mode between the cassette and the console device is switchable between a wired mode and a wireless mode. Due to shortage of a battery of the cassette, the communication mode is switched to the wired mode to start charging the battery and send image data from the cassette to the console device through a cable. The console device has first and second judging sections. The first judging section judges whether or not a charge level of the battery exceeds a predetermined threshold value. The second judging section judges whether or not radiography is in progress. If it is judged that the charge level of the battery exceeds the predetermined threshold value and the radiography is not in progress, a window that indicates permission for switching to the wireless mode is displayed on a monitor.

9 Claims, 8 Drawing Sheets

(56) References Cited

U.S. PATENT DOCUMENTS

| | | | |
|---|---|---|---|
| 5,745,487 A * | 4/1998 | Hamaki | 370/352 |
| 6,628,201 B2 * | 9/2003 | Cho et al. | 340/600 |
| 7,041,512 B2 * | 5/2006 | Fujiyoshi et al. | 438/5 |
| 7,690,570 B2 * | 4/2010 | Fruhauf | 235/451 |
| 7,767,981 B2 * | 8/2010 | Kuwabara et al. | 250/484.4 |
| 7,807,974 B2 * | 10/2010 | Ishitsu et al. | 250/363.04 |
| 7,899,401 B2 * | 3/2011 | Tanaka et al. | 455/67.11 |
| 7,909,511 B2 * | 3/2011 | Hall | 378/189 |
| 7,952,080 B2 * | 5/2011 | Kuwabara et al. | 250/484.4 |
| 7,977,644 B2 * | 7/2011 | Kito | 250/370.09 |
| 7,985,955 B2 * | 7/2011 | Ohta et al. | 250/370.09 |
| 8,121,532 B2 * | 2/2012 | Huang | 455/1 |
| 8,330,597 B2 * | 12/2012 | Nishino et al. | 340/540 |
| 2006/0017028 A1 * | 1/2006 | Ohara et al. | 250/580 |
| 2006/0202127 A1 | 9/2006 | Ozeki | |
| 2009/0189761 A1 * | 7/2009 | Nishino et al. | 340/540 |
| 2010/0156590 A1 * | 6/2010 | Kyllonen et al. | 340/3.1 |
| 2010/0232575 A1 * | 9/2010 | Hall | 378/189 |
| 2010/0271215 A1 * | 10/2010 | Ohta et al. | 340/600 |
| 2010/0283583 A1 * | 11/2010 | Ohta et al. | 340/10.1 |
| 2012/0206233 A1 * | 8/2012 | Kamiya et al. | 340/2.1 |

FOREIGN PATENT DOCUMENTS

| | | |
|---|---|---|
| JP | 2005-006979 | 1/2005 |
| JP | 2005-208269 A | 8/2005 |
| JP | 2008-134057 A | 6/2008 |
| JP | 2009-201968 A | 9/2009 |
| JP | 2009-297187 | 12/2009 |

* cited by examiner

RADIATION IMAGING SYSTEM HAVING RADIATION IMAGING CASSETTE AND CONSOLE DEVICE, AND RADIATION IMAGING PROGRAM

CROSS-REFERENCE TO RELATED APPLICATIONS

The present application claims priority from Japanese Patent Application No. 2010-058608, filed Mar. 16, 2010, the contents of which are herein incorporated by reference in their entirety.

BACKGROUND OF THE INVENTION

1. Field of the Invention

The present invention relates to a radiation imaging system having a console device and a radiation imaging cassette that contains a flat panel detector in a cassette casing, and a radiation imaging program.

2. Description Related to the Prior Art

In a medical field, a radiation imaging system that uses radiation such as X-rays is widely known. The radiation imaging system is constituted of a radiation generation device for applying the radiation to a patient's body part to be examined, and a radiation detector for detecting the radiation that has passed through the body part. As the radiation detector, an IP cassette containing an imaging plate (IP) and a flat panel detector (FPD), which has the advantage that can directly convert the radiation into image data, are in practical use. Moreover, a portable FPD cassette that contains the FPD in a casing of the same shape and size as that of the IP cassette is recently developed to allow loading of the FPD on the conventional radiation imaging system.

For example, Japanese Patent Laid-Open Publication Nos. 2009-297187 and 2005-006979 disclose the radiation imaging system that is provided with the FPD cassette having a battery and an antenna and a console device for communicating with the FPD cassette by wireless. Besides, a cable is connectable between the FPD cassette and the console device, to carry out communication and charge of the battery thereby.

In this radiation imaging system, a communication mode of the image data from the FPD cassette to the console device is selectively switchable between a wireless mode and a wired mode as occasion demands. The wireless mode is selected in the case of giving high priority to flexibility in handling of the FPD cassette, while the wired mode is selected in the case of giving high priority to stability in communication.

When the wireless mode is selected, the battery supplies the FPD cassette with drive power. If the FPD cassette has almost run out of the battery and loses the ability of sending the image data by wireless, switching from the wireless mode to the wired mode allows the FPD cassette to send the image data through the cable. Also, the FPD cassette can get the drive power and charge the battery through the cable.

The FPD cassette is generally used in the wireless mode without plugging the cable from a handling viewpoint. However, as described above, when the FPD cassette is almost run out of the battery or is used in an unstable communication environment such as a ward of a hospital, a doctor sometimes plugs the cable to switch from the wireless mode to the wired mode as a temporary measure.

In such a case, it is desirable to return the communication mode from the wired mode to the wireless mode as soon as the battery charge is completed or a communication condition is recovered. However, the doctor cannot know the time of completion of the battery charge or recovery of the communication condition. If the cable is unplugged while the radiation imaging system processes data through the cable, operation of the system becomes unstable. Especially, in the system that follows an operation sequence in which a preview image is sent before sending an actual image, the doctor tends to have wrong idea that all processes have been completed at the time of checking the preview image, and hence easily unplugs the cable during transmission of the actual image.

The majority of doctors want to switch the communication mode at a break of radiography. Taking the case of successively carrying out the radiography of plural patients as an example, if the doctor knows that the communication mode is switchable to the wireless mode in the middle of the radiography of the certain patient, the doctor often makes continuation of the radiography a higher priority than switching of the communication mode. At the time of finishing the radiography of that patient, the doctor easily forgets about switching to the wireless mode and starts the radiography of the next patient. As a result, the doctor easily loses an opportunity for return to the wireless mode.

SUMMARY OF THE INVENTION

An object of the present invention is to provide a radiation imaging system that can easily notify a doctor of permission of switching from a wired mode to a wireless mode at a time appropriate for maintaining stability of the system.

To achieve the above and other objects of the present invention, a radiation imaging system according to the present invention includes a first judging section, a second judging section, and a notification section. The first judging section judges whether or not a wireless mode is selectable based on at least one of a charge level of a battery and a condition of wireless communication. The second judging section judges whether or not radiography is completed. If the first judging section judges that the wireless mode is selectable, the notification section makes a notification of permission for selecting the wireless mode in timing based on a judgment result of the second judging section.

The console device may include a storage unit for storing an image sent from the radiation imaging cassette. The second judging section may judge whether or not radiography is completed on a patient-by-patient basis. The notification section may make the notification at a time of completing the radiography of the single patient.

When every image related to the single patient is completely transmitted from the radiation imaging cassette to the console device, the radiography of the patient may be judged to be completed.

In the storage unit, a radiography order registered on a patient-by-patient basis and status information of the radiography order may be stored in relation to each other. The status information represents whether or not the radiography corresponding to the radiography order is completed. The second judging section may judge based on the status information whether or not the radiography of the patient is completed.

If the charge level of the battery exceeds a predetermined threshold value, the first judging section may judge that the wireless mode is selectable.

It is preferable that the notification section includes a monitor provided in the console device.

The first judging section, the second judging section, and the notification section as described above may be provided in the console device or the radiation imaging cassette.

A radiation imaging program according to the present invention makes a computer of the console device execute the steps of judging whether or not the wireless mode is selectable based on at least one of the charge level of the battery and the condition of the wireless communication, judging whether or not the radiography is completed, and making the notification of the permission for selecting the wireless mode at the time of completing the radiography, if the wireless mode is judged to be selectable.

According to the present invention, in the radiation imaging cassette that is switchable between the wireless mode and the wired mode, the charge level of the battery is measured. If the radiation imaging cassette is judged to be switchable to the wireless mode, the notification section indicates the permission for switching to the wireless mode at the time of completing the radiography of the single patient. Thus, a doctor is easily notified of the permission, and stably switches the system to the wireless mode.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

First Embodiment

Figure 1:
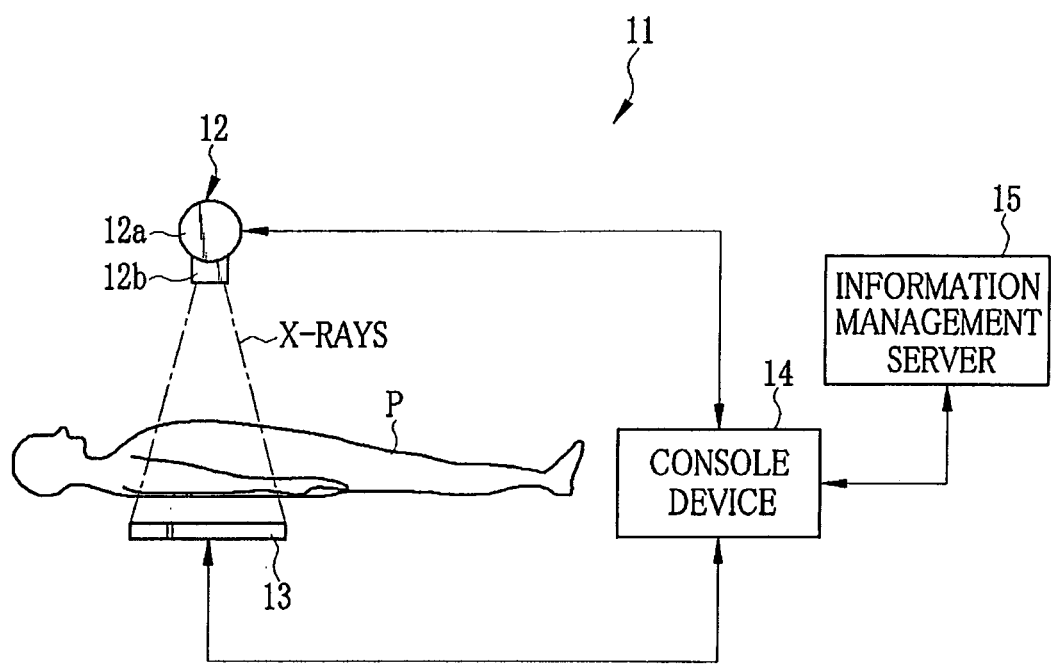
FIG. 1 is a schematic view of a radiation imaging system.

As shown in FIG. 1, a radiation imaging system 11 according to a first embodiment is constituted of a radiation generation device 12, an FPD cassette (hereinafter simply called cassette) 13, a console device 14, and an information management server 15. The radiation generation device 12 applies radiation such as X-rays to a body part to be examined of a patient P. The cassette 13 detects the X-rays that have passed through the body part. The console device 14 controls the radiation generation device 12 and the cassette 13. The information management server 15 manages an order of radiography on a patient-by-patient basis. The radiation generation device 12 and the cassette 13 are set up in a radiation shielded chamber or room, while the console device 14 and the information management server 15 are set up in an operation room next to the radiation shielded chamber.

The radiation generation device 12 is constituted of an X-ray tube 12a for generating the X-rays, and a collimator 12b for limiting an irradiation field of the X-rays, for example. The radiation generation device 12 is movably supported by a support member (not illustrated). The radiation generation device 12 is moved by the support member so as to face the cassette 13, and the irradiation field of the X-rays is varied in accordance with the body part to be examined, which is set by the console device 14.

Figure 2:
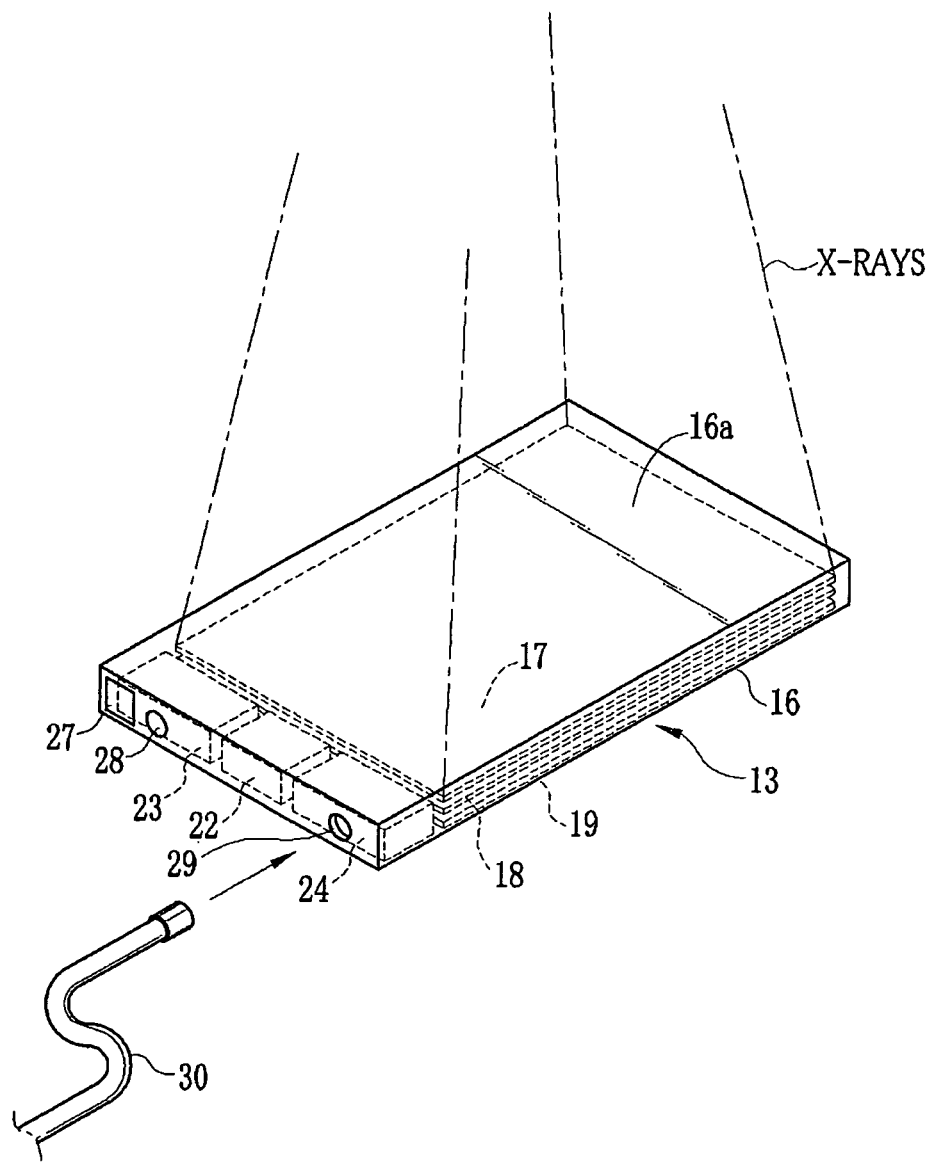
FIG. 2 is a perspective view of an FPD cassette.

As shown in FIG. 2, the cassette 13 has the same shape and size as those of a conventional cassette containing an imaging plate (IP) to offer high handleability and portability. Besides being used in the radiation shielded chamber, the cassette 13 is sometimes brought out of the radiation shielded chamber together with a portable radiation imaging system for use in a consulting room, a ward of a hospital, or the like.

The cassette 13 is provided with a cassette casing 16 made of a radiation transparent material. The casing 16 contains a grid 17, a radiation detector 18, and a lead plate 19 that are disposed in this order from a side of a radiation incident surface 16a, upon which the X-rays are incident. The grid 17 removes a scattering of the X-rays by the patient's body. The radiation detector 18 detects the X-rays that have passed through the body part to be examined. The lead plate 19 absorbs a backward scattering of the X-rays.

The radiation detector 18 is an indirect conversion flat panel detector (FPD) having a phosphor layer and a detecting element layer. The phosphor layer is made of a phosphor such as CsI (cesium iodide), and converts the incident X-rays into visible light. The detecting element layer is a two-dimensional sensor matrix of pixels. Each pixel is composed of a photodiode for converting the visible light generated in the phosphor layer into electric charge and accumulating the electric charge, and a TFT (thin film transistor) switch for reading out the electric charge from the photodiode. Otherwise, the radiation detector 18 may be a direction conversion FPD, in which a conversion layer made of amorphous selenium or the like directly converts the radiation into the electric charge.

The casing 16 contains a control unit 22, a power unit 23, and a communication unit 24 in addition to above. The power unit 23 feeds electric power to each part of the cassette 13. The control unit 22 controls operation of the radiation detector 18. The communication unit 24 communicates with the console device 14 to send and receive various types of data including image data.

On a side surface of the casing 16, there are provided a power switch 27, a monitor lamp 28, and a connector 29. The power switch 27 powers the cassette 13 on and off. The monitor lamp 28 indicates a power state of the cassette 13 and a charge state of a battery 36. The connector 29 is provided with a power receiving terminal 31 and a communication terminal 32 (see both of them in FIG. 3). When a cable 30 connected to the console device 14 is plugged in the power receiving terminal 31 and the communication terminal 32, electric power is supply to the cassette 13 via the power receiving terminal 31, and communication is established between the console device 14 and the cassette 13 via the communication terminal 32.

Figure 3:
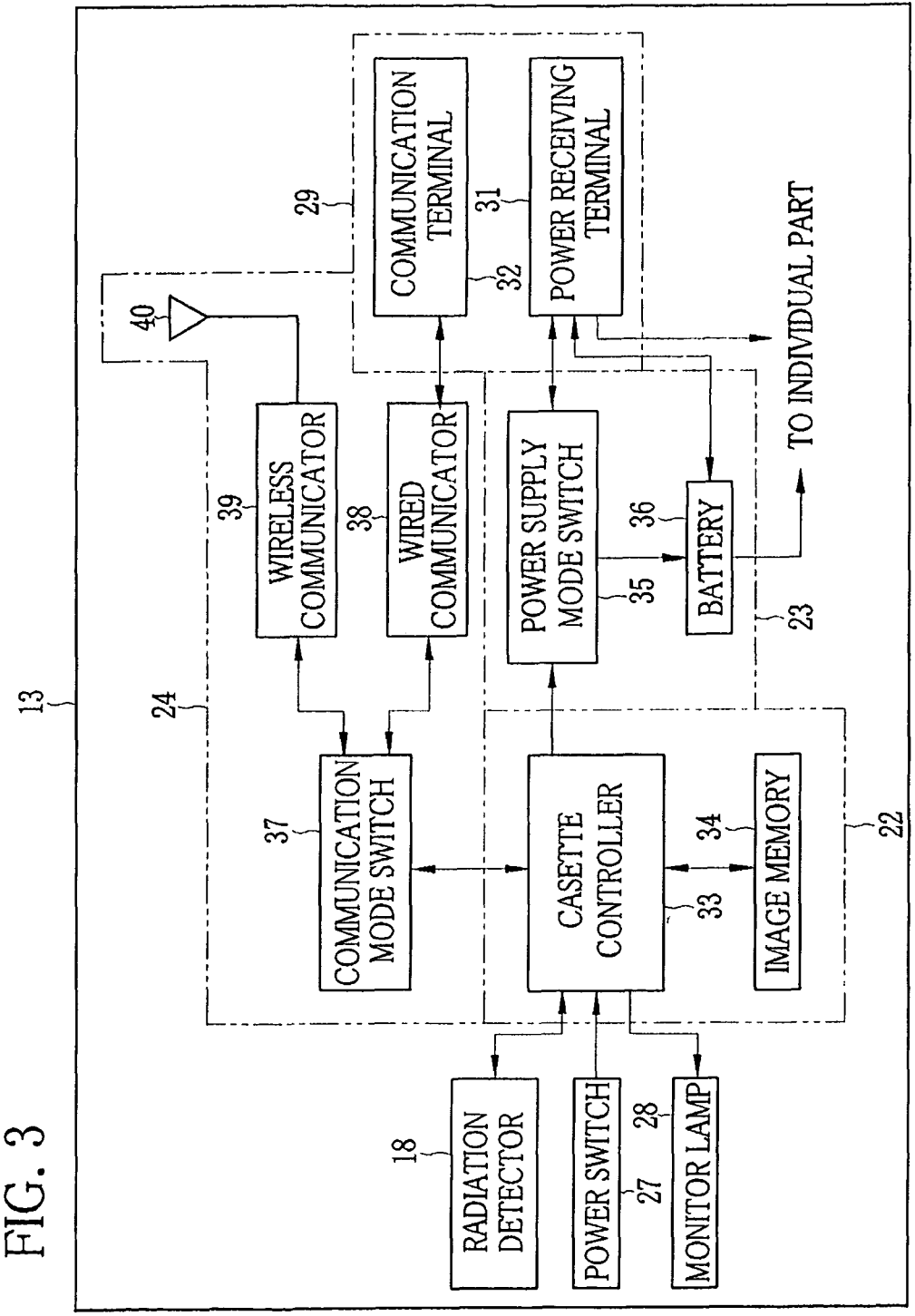
FIG. 3 is a block diagram of the FPD cassette.

As shown in FIG. 3, the control unit 22 is provided with a cassette controller 33 and an image memory 34. The cassette controller 33 includes a CPU for carrying out various types of computing processing, a ROM for storing control programs and control data executed by the CPU, and a RAM used as a working memory of the CPU by a load of the programs and data, and overall controls each part of the cassette 13. The image memory 34 stores the image data outputted from the radiation detector 18.

The power unit 23 is provided with a power supply mode switch 35 and a battery 36. The power supply mode switch 35 switches a mode of supplying electric power to each part of the cassette 13 between a battery mode and a wired mode. In the battery mode, the electric power is supplied from the battery 36. In the wired mode, the electric power is supplied from the console device 14 through the power receiving terminal 31. The power supply mode switch 35 selects the battery mode if no electric power is supplied through the power receiving terminal 31, while the power supply mode switch 35 selects the wired mode if the electric power is supplied through the power receiving terminal 31. The battery 36 is charged with the electric power supplied through the power receiving terminal 31.

The communication unit 24 is provided with a communication mode switch 37, a wired communicator 38, a wireless communicator 39, and an antenna 40. The communication mode switch 37 switches a communication mode with the console device 14 between a wired mode using the cable 30 and a wireless mode using the antenna 40. The communication mode switch 37 selects the wired mode, if the cable 30 is connected to the communication terminal 32. The communication mode switch 37 selects the wireless mode, if the cable 30 is disconnected to the communication terminal 32. The wired communicator 38 establishes communication with the console device 14 in the wired mode through the cable 30 connected to the communication terminal 32. The wireless communicator 39 establishes communication with the console device 14 in the wireless mode via the antenna 40.

Figure 4:
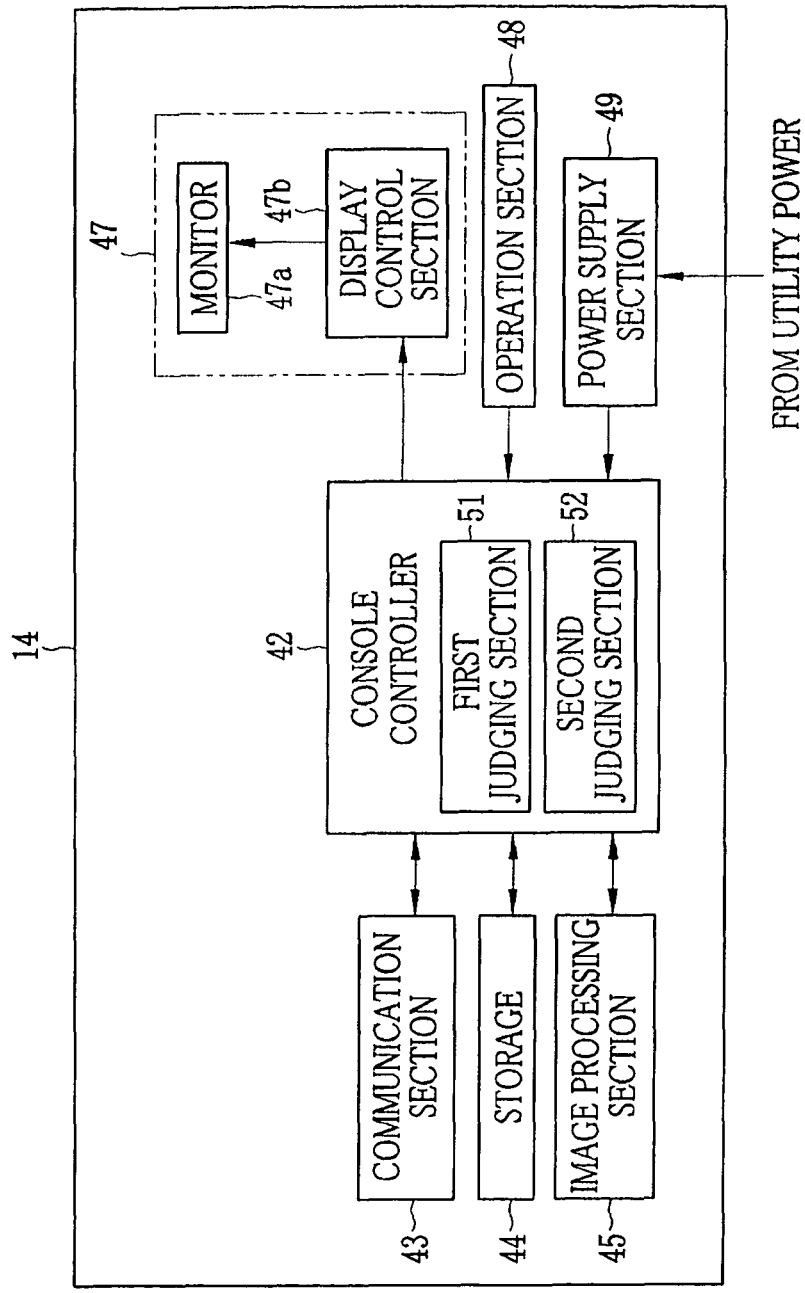
FIG. 4 is a block diagram of a console device.

As shown in FIG. 4, the console device 14 is provided with a console controller 42, a communication section 43, storage 44, an image processing section 45, a display section 47, an operation section 48, and a power supply section 49.

As with the cassette controller 33, the console controller 42 includes a CPU for carrying out various types of computing processing, a ROM for storing control programs and control data executed by the CPU, and a RAM used as a working memory of the CPU by a load of the programs and data, and overall controls each part of the console device 14.

The communication section 43 establishes communication with the radiation generation device 12, the cassette 13, and the information management server 15, to send and receive various types of data. The communication section 43 communicates with the cassette 13 in the wired mode, if the cassette 13 is connected through the cable 30. The communication section 43 communicates with the cassette 13 through an antenna (not illustrated) in the wireless mode, if the cassette 13 is disconnected.

Figure 5A:
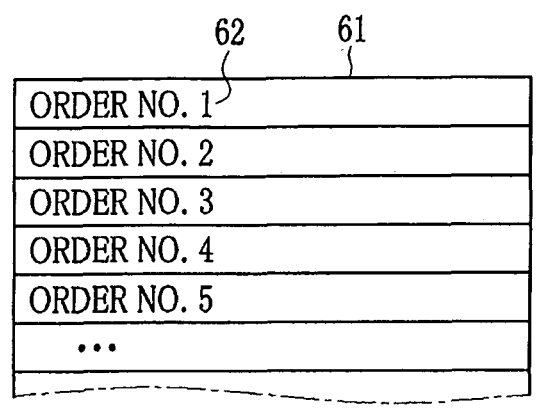
FIG. 5A is an explanatory view of an order table.
Figure 5B:
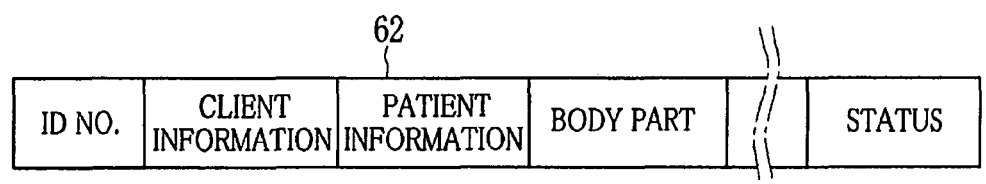
FIG. 5B is an explanatory view of each order.

The storage 44 stores an order table 61 as shown in FIG. 5A. In the order table 61, orders 62 sent from the information management server 15 are listed in reception order. As shown in FIG. 5B, each order 62 includes items of an ID number, client information (for example, a diagnosis and treatment department name and a doctor's name), patient information (for example, a patient's name and age), the body part to be examined, a status (waiting, in progress, or finished), and the like. Each item is entered during reception of the order 62. At the time of receiving the order 62, "waiting" is entered in the status. Then, the status is changed to "in progress" upon starting the radiography. After that, the status is changed to "finished" upon completion of the radiography, in other words, at the time of completing transmission of all the image data of the single order from the cassette 13.

Returning to FIG. 4, the image processing section 45 applies various types of image processing to the image data received from the cassette 13. The image data after the image processing is written to the storage 44, while being associated with the order 62. The display section 47 includes a monitor 47a such as an LCD, and a display control section 47b for displaying on the monitor 47a a radiographic image, various operation screens including a radiographic operation menu, and the like. The radiographic operation menu displayed on the monitor 47a includes the orders 62 listed in the order table 61.

The operation section 48 includes a keyboard, a mouse, and the like (all of them are not illustrated), for use in various settings and operations. The operation section 48 also includes a shutter button. Upon a press of the shutter button, the radiation generation device 12 applies the X-rays, and the cassette 13 detects the X-rays. The doctor carries out the radiography by manipulating the operation section 48 with following the orders 62 and the like displayed on the monitor 47a.

The power supply section 49 receives the electric power from outside utility power, and distributes the electric power to each part of the console device 14. If the cassette 13 is connected to the console device 14 through the cable 30, the power supply section 49 feeds the electric power to the cassette 13.

If the cassette 13 is connected to the console device 14 through the cable 30, the console controller 42 measures a charge level of the battery 36. The console controller 42 functions as a first judging section 51 that judges whether or not the charge level of the battery 36 exceeds a predetermined threshold value (for example, 80% of full charge), and a second judging section 52 that refers to the status of the orders 62 listed in the order table 61 and judges whether or not the radiography is in the progress.

If one of the orders 62 has the status of "in progress", the second judging section 52 judges that the radiography is in progress. If no order 62 has the status of "in progress", in other words, if every order 62 has the status of "finished" or "waiting", the second judging section 52 judges that the radiography is not in progress.

The display control section 47b displays on the monitor 47a whether or not the communication mode is switchable from the wired mode to the wireless mode, based on judgment results of the first and second judging sections 51 and 52.

Figure 6A:
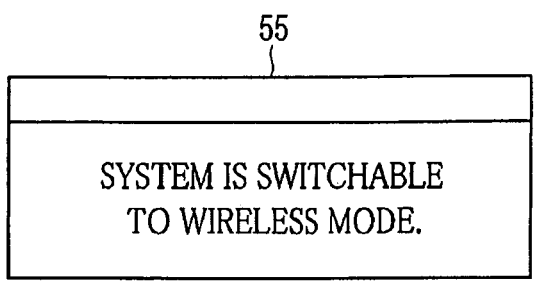
FIG. 6A is an explanatory view of a window that makes notification of permission for switching to a wireless mode.

If the first judging section 51 judges that the charge level of the battery 36 exceeds the predetermined threshold value, and the second judging section 52 judges that the radiography is not in progress, the display control section 47b displays on the monitor 47a a window 55, which says that the communication mode is switchable to the wireless mode, as shown in FIG. 6A.

Figure 6B:
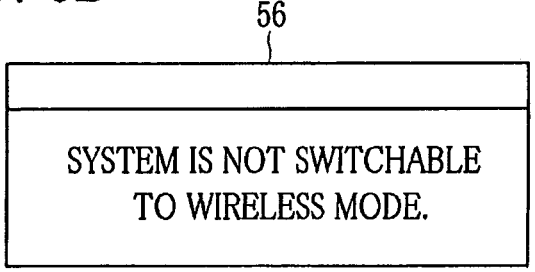
FIG. 6B is an explanatory view of a window that makes notification of prohibition of switching to the wireless mode.

If the first judging section 51 judges that the charge level of the battery 36 is the predetermined threshold value or less, and the second judging section 52 judges that the radiography is not in progress, the display control section 47b displays on the monitor 47a a window 56, which says that the communication mode is not switchable to the wireless mode, as shown in FIG. 6B.

Figure 7:
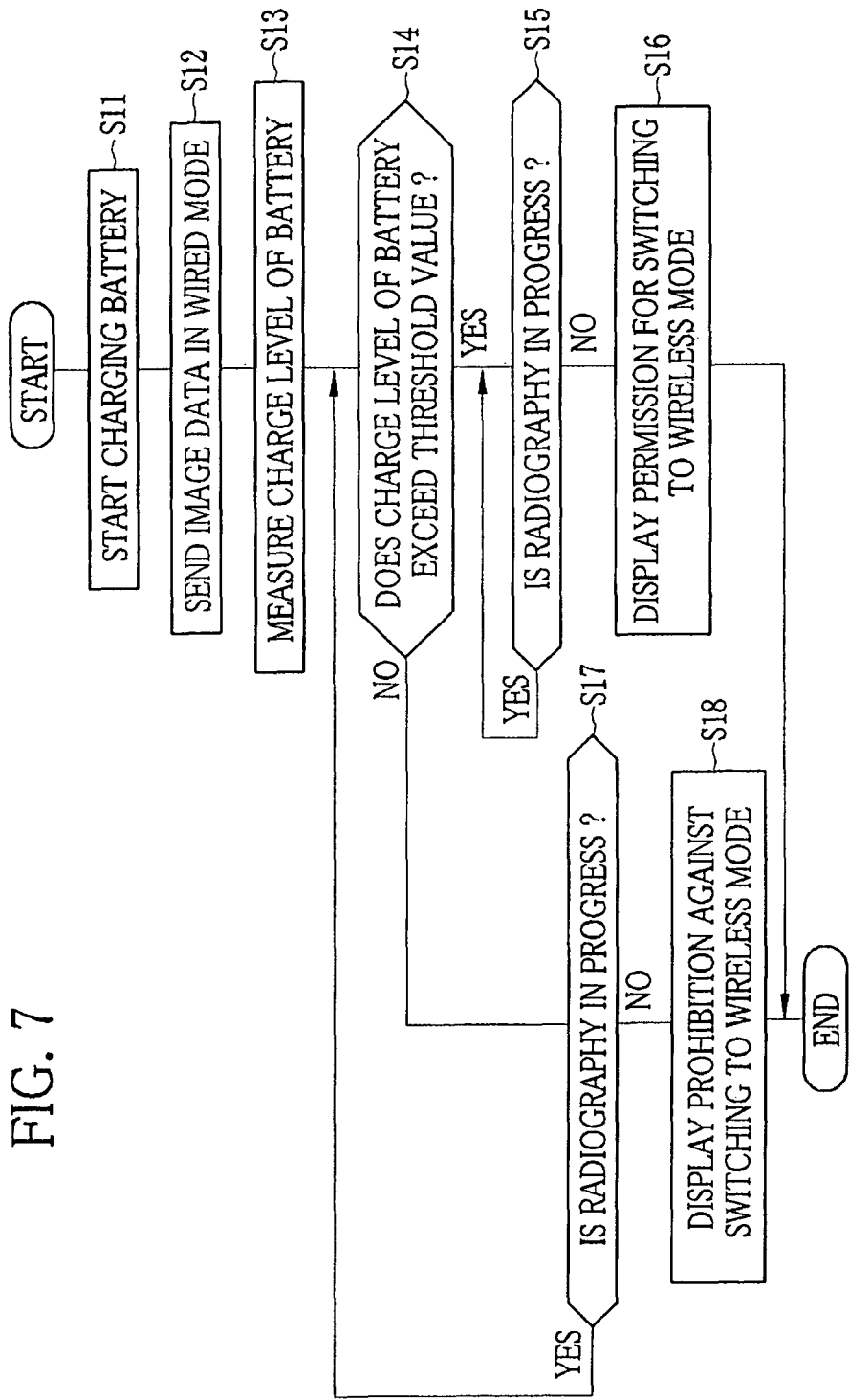
FIG. 7 is a flowchart of the radiation imaging system according to a first embodiment.

Next, operation of the radiation imaging system 11 will be described with referring to FIG. 7. When the cassette 13 has almost run out of the battery 36 and is no longer able to send the image data by wireless, the cable 30 is plugged into the connector 29 to start charging the battery 36 (S11) and send the image data in the wired mode (S12).

The first judging section 51 measures the charge level of the battery 36 (S13), and judges whether or not the charge level of the battery 36 exceeds the predetermined threshold value (S14).

If it is judged that the charge level of the battery 36 exceeds the predetermined threshold value (YES in S14), the second judging section 52 judges whether or not the radiography, which is carried out on a patient-by-patient basis, is in progress (S15). If it is judged that the radiography is not in progress (NO in S15), the window 55 (see FIG. 6A) saying that the communication mode is switchable to the wireless mode is displayed on the monitor 47a (S16).

Even if it is judged that the charge level of the battery 36 does not exceed the predetermined threshold value (NO in S14), the second judging section 52 judges whether or not the radiography is in progress (S17). If it is judged that the radiography is not in progress (NO in S17), the window 56 (see FIG. 6B) saying that the communication mode is not switchable to the wireless mode is displayed on the monitor 47a (S18).

As described above, in the radiation imaging system 11 that successively carries out the radiography on a patient-by-patient basis, after the communication mode is switched due to shortage of the charge level of the battery 36 from the wireless mode to the wired mode to start charging the battery 36, if the charge level of the battery 36 exceeds the predetermined threshold value so as to be adequate for returning to the wireless mode, the second judging section 52 judges whether or not the radiography is in progress. If the radiography is not judged to be in progress, the window 55 indicating permission for switching to the wireless mode is displayed on the monitor 47a, on which the radiographic image is to be displayed. Thus, it is possible to notify the doctor of the permission for switching at an appropriate time without interrupting checking operation of the radiographic image. This does not impose an inconvenience on the doctor. Also, the doctor is easily notified of the permission, and does not miss a chance to switch to the wireless mode.

Also, the radiography is not judged to be in progress at the time of completing transmission of all the image data of the single order (single patient), in other words, at the time of completing the checking operation of the radiographic image, and then the window 55 is displayed on the monitor 47a. Thus, it is possible to display the permission for switching to the wireless mode, while the doctor is watching the monitor 47a. The doctor is not busy during the time from completion of the radiography of one patient until starting the radiography of the next patient. Therefore, the doctor can efficiently switch the cassette 13 to the wireless mode with sufficient time.

Second Embodiment

In a second embodiment, the notification of the permission or prohibition of switching to the wireless mode is made in consideration of a communication condition in the wireless mode, in addition to the charge level of the battery 36. The same structure, operation, and effect as those of the first embodiment will be omitted.

In addition to the function of the first embodiment, the first judging section 51 according to the second embodiment checks the communication condition (for example, communication signal strength) between the cassette 13 and the console device 14 in the wireless mode, in order to judge whether or not the communication condition is good enough for sending the image data.

If the first judging section 51 judges that the charge level of the battery 36 exceeds the predetermined threshold value and the cassette 13 and the console device 14 are in the good communication condition (good enough for sending the image data) in the wireless mode, and the second judging section 52 judges that the radiography is not in progress, the display control section 47b displays the window 55 as shown in FIG. 6A on the monitor 47a.

If nevertheless the second judging section 52 judges that the radiography is not in progress, the first judging section 51 judges that the charge level of the battery 36 does not exceed the predetermined threshold value or the cassette 13 and the console device 14 are not in the good communication condition (not good enough for sending the image data) in the wireless mode, the display control section 47b displays the window 56 as shown in FIG. 6B on the monitor 47a.

Figure 8:
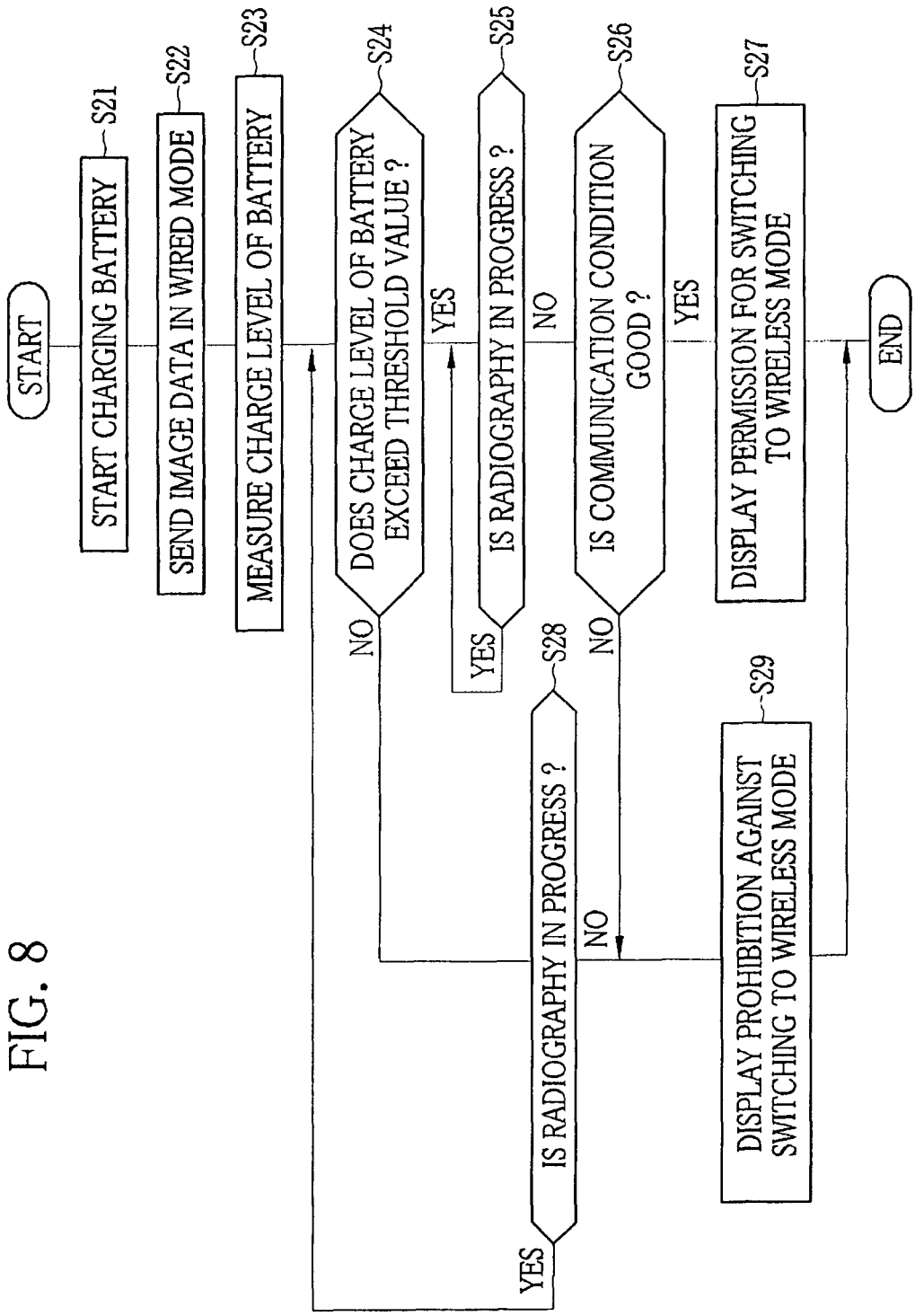
FIG. 8 is a flowchart of the radiation imaging system according to a second embodiment.

Next, operation of the radiation imaging system 11 according to the second embodiment will be described with referring to FIG. 8. S21 to S25 are the same as S11 to S15. In S25, if the radiography is not judged to be in progress (NO in S25), the first judging section 51 checks the radio signal strength communicated between the cassette 13 and the console device 14, to judge whether or not the communication condition is good enough for sending the image data (S26).

If the communication condition is judged to be good (YES in S26), the window 55 (see FIG. 6A) indicating the permission for switching to the wireless mode is displayed on the monitor 47a (S27).

If it is judged that the charge level of the battery 36 does not exceed the predetermined threshold value (NO in S24), the operation goes to S28 and S29. S28 and S29 are the same as S17 and S18.

If it is judged that the communication condition is not good (NO in S26), the window 56 (see FIG. 6B) indicating the prohibition against switching to the wireless mode is displayed on the monitor 47a (S29).

In the above embodiments, the console controller 42 of the console device 14 includes the first and second judging sections 51 and 52. However, the cassette controller 33 of the cassette 13 may function as similar judging sections.

In the above embodiments, the doctor is notified of the permission for switching to the wireless mode by the window 55 displayed on the monitor 47a, but may be notified by blinking the monitor lamp 28 provided in the cassette 13 or a monitor lamp (not illustrated) provided in the console device 14, or by outputting sound from a speaker (not illustrated) additionally provided in the console device 14.

In the above embodiments, the status is changed to "finished", upon completion of sending all the image data of the single order. However, in a case where the single order directs the radiography of plural images, the status may be changed to "finished" whenever the radiography of each image is completed. Whenever the status is changed to "finished", the window 55 indicating the permission for switching to the wireless mode may be displayed on the monitor 47a. This facilitates early return to the wireless mode.

In the above embodiments, the present invention is applied to the X-ray imaging system using the X-rays as the radiation, but the present invention is applicable to the other types of radiation imaging systems using gamma rays, alpha rays, or the like.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:
1. A radiation imaging system comprising:
a radiation imaging cassette;
a console device for controlling the radiation imaging cassette, the radiation imaging cassette having a battery and an antenna used in wireless communication and a connector detachably connected to a cable used in wired communication;
a communication mode between the radiation imaging cassette and the console device being switchable between a wired mode and a wireless mode;

a first judging section for judging whether or not the wireless mode is selectable based on at least one of a charge level of the battery and a condition of the wireless communication;

a second judging section for judging whether or not radiography is completed; and a notification section for making a notification of permission for selecting the wireless mode in timing based on a judgment result of the second judging section, if the first judging section judges that the wireless mode is selectable.

2. The radiation imaging system according to claim 1, wherein the console device includes a storage unit for storing an image sent from the radiation imaging cassette;

wherein the second judging section judges whether or not the radiography is completed on a patient-by-patient basis; and wherein the notification section makes the notification at a time of completing the radiography of the single patient.

3. The radiation imaging system according to claim 2, wherein when every image related to the single patient is completely transmitted from the radiation imaging cassette to the console device, the radiography of the patient is judged to be completed.

4. The radiation imaging system according to claim 3, wherein in the storage unit, a radiography order registered on a patient-by-patient basis and status information of the radiography order are stored in relation to each other, and the status information represents whether or not the radiography corresponding to the radiography order is completed; and wherein the second judging section judges based on the status information whether or not the radiography of the patient is completed.

5. The radiation imaging system according to claim 1, wherein the first judging section judges that the wireless mode is selectable, if the charge level of the battery exceeds a predetermined threshold value.

6. The radiation imaging system according to claim 1, wherein the notification section includes a monitor provided in the console device.

7. A console device comprising:

a radiation imaging cassette which communicates with the console device in a switchable manner between a wired mode and a wireless mode, the radiation imaging cassette having a battery and an antenna used in wireless communication;

a connector detachably connected to a cable used in wired communication;

a first judging section for judging whether or not the wireless mode is selectable based on at least one of a charge level of the battery and a condition of the wireless communication;

a second judging section for judging whether or not radiography is completed; and a notification section for making a notification of permission for selecting the wireless mode in timing based on a judgment result of the second judging section, if the first judging section judges that the wireless mode is selectable.

8. A radiation imaging cassette comprising:

a battery and an antenna used in wireless communication;

a connector detachably connected to a cable used in wired communication, the radiation imaging cassette communicating with a console device in a switchable manner between a wired mode and a wireless mode;

a first judging section for judging whether or not the wireless mode is selectable based on at least one of a charge level of the battery and a condition of the wireless communication;

a second judging section for judging whether or not radiography is completed; and a notification section for making a notification of permission for selecting the wireless mode in timing based on a judgment result of the second judging section, if the first judging section judges that the wireless mode is selectable.

9. A non-transitory radiation imaging program installed on a computer of a console device, the radiation imaging program making the computer execute the steps of:

communicating the console device with a radiation imaging cassette in a switchable manner between a wired mode and a wireless mode, the radiation imaging cassette having a battery and an antenna used in wireless communication and a connector detachably connected to a cable used in wired communication;

judging whether or not the wireless mode is selectable based on at least one of a charge level of the battery and a condition of the wireless communication;

judging whether or not radiography is completed; and making a notification of permission for selecting the wireless mode at a time of completing the radiography, if the wireless mode is judged to be selectable.

* * * * *